(12) United States Patent
Kligerman (10) Patent No.: US 8,802,073 B2
(45) Date of Patent: Aug. 12, 2014

(54) METHODS AND COMPOSITIONS FOR WOUND HEALING

(75) Inventor: Alan E. Kligerman, Egg Harbor Township, NJ (US)

(73) Assignee: Prelief Inc., Egg Harbor Township, NJ (US)

( * ) Notice: Subject to any disclaimer, the term of this patent is extended or adjusted under 35 U.S.C. 154(b) by 244 days.

(21) Appl. No.: 12/740,510

(22) PCT Filed: Nov. 12, 2008

(86) PCT No.: PCT/US2008/012704
§ 371 (c)(1),
(2), (4) Date: Apr. 29, 2010

(87) PCT Pub. No.: WO2009/064412
PCT Pub. Date: May 22, 2009

(65) Prior Publication Data
US 2010/0239645 A1   Sep. 23, 2010

Related U.S. Application Data

(60) Provisional application No. 60/988,128, filed on Nov. 15, 2007, provisional application No. 61/133,687, filed on Jul. 1, 2008.

(51) Int. Cl.
*A61K 31/74* (2006.01)
*A01N 57/10* (2006.01)
*A61K 31/66* (2006.01)

(52) U.S. Cl.
USPC ........................................ 424/78.06; 514/143

(58) Field of Classification Search
USPC ........................................ 424/78.06; 514/143
See application file for complete search history.

(56) References Cited

U.S. PATENT DOCUMENTS

| | | | |
|---|---|---|---|
| 4,001,413 A | 1/1977 | Adams et al. | |
| 5,271,939 A | 12/1993 | Robertson et al. | |
| 5,674,912 A * | 10/1997 | Martin | 514/724 |
| 5,885,597 A | 3/1999 | Botknecht et al. | |
| 5,972,321 A * | 10/1999 | Kligerman et al. | 424/65 |
| 6,214,889 B1 * | 4/2001 | Peterson et al. | 514/557 |
| 2002/0157972 A1 | 10/2002 | Gallo et al. | |
| 2004/0037766 A1 * | 2/2004 | Kligerman et al. | 423/299 |

FOREIGN PATENT DOCUMENTS

DE       19859611       *  6/2000

OTHER PUBLICATIONS

Atiyeh et al. Aest. Plast. Surg. 2003, 27, 411-417.*
Dohman, Surgical Infections, Jan. 2006, 7 (S1), S13-S17.*
English Machine Translation of DE 19859611 (published: Jun. 2000).*
Int'l Search Report and Written Opinion dated Jan. 13, 2009 in Int'l Appln No. PCT/US2008/012704.

* cited by examiner

*Primary Examiner* — Gina C Justice
*Assistant Examiner* — Genevieve S Alley
(74) *Attorney, Agent, or Firm* — Panitch Schwarze Belisario & Nadel LLP (57) ABSTRACT

Glycerophosphate salts have been found to hasten the healing of wounds and minimize the formation of scars, particularly when it is first applied to a wound about 0 to about 7 days after the wound is inflicted. Methods and compositions are provided for treating wounds using a composition comprising an effective amount of glycerophosphate salt. In particular, methods are provided for treating wounds using calcium glycerophosphate (CGP), for accelerating the healing process, reducing pain and scar formation, and for the cosmetic reducing, excision, erasure and/or complete repair of scars (scar revision).

5 Claims, 6 Drawing Sheets

METHODS AND COMPOSITIONS FOR WOUND HEALING

CROSS-REFERENCE TO RELATED APPLICATION

This application is a Section 371 of International Application No. PCT/US2008/012704, filed Nov. 12, 2008, which was published in the English language on May 22, 2009 under International Publication No. WO 2009/064412 A1, which claims the benefit of U.S. Provisional Patent Application No. 60/988,128, filed Nov. 15, 2007 and U.S. Provisional Patent Application No. 61/133,687, filed Jul. 1, 2008, the disclosures of which are incorporated herein by reference.

BACKGROUND OF THE INVENTION

Wound healing is a process of regenerating dermal and epidermal tissues to repair a wound. This process is complex, involving several phases, such as the vascular reaction and blood clotting, inflammatory, proliferative and remodeling phases. These phases overlap and are partly mutually dependent, so that the sequence only approximately corresponds to the time course of wound healing.

The vascular reaction prevents major blood losses and entails vasoconstriction, which persists until blood clotting provisionally closes the wound. In the inflammatory phase, increased numbers of blood cells such as granulocytes, macrophages and lymphocytes, are brought to the area at or near the wound. The blood cells clean the wound by taking up exogenous materials and tissue detritus and breaking them down enzymatically.

Collagen deposition, granulation tissue formation, epithelialization and wound contraction occur in the proliferative phase. For example, new blood vessels are formed (angiogenesis) from as early as the third day after the injury to provide adequate blood supply for wound healing. New connective tissue formation takes place in parallel with the vascularization. Fibroblasts migrate along the fibrin matrix into the wound. They produce the connective tissue ground substance consisting of proteoglycans and collagen fibers, which are crucial for tissue strength. In the maturation and remodeling phase, collagen fibers are remodeled and realigned along tension lines and cells that are no longer needed are removed by apoptosis.

Scars are areas of fibrous tissue that replace normal tissues destroyed by a wound. Scar tissue is not identical to the normal tissue and is often of inferior functional quality. For example, scars in the skin can be less resistant to ultraviolet radiation, and may contain no sweat glands and hair follicles. Importantly, scar tissue never achieves the essential flexibility of normal epidermal tissue and therefore presents not only cosmetic issues but also chronic mechanical problems. Scarring is a natural part of the wound healing process. With the exception of very minor lesions, every wound (e.g. after accident, disease, or surgery) results in some degree of scarring.

Wound healing requires a balanced equilibrium of contrary actions such as cell proliferation and cell apoptosis, construction and breakdown of blood vessels, and construction and breakdown of collagen. Disturbance of the equilibrium may lead to the formation of chronic wounds, which may never heal or heal at slower rate, and/or increased scar formation. Also, "permanentized" scar tissue composed of fibroblastic cells may form, which frequently results in keloids, a type of scar resulting from an overgrowth of tissue at the site of a healed skin injury. Keloids are unsightly and problematic firm surface tissue of different coloration and different and poorer qualities. They are rubbery lesions or shiny, fibrous nodules, having a color from pink to flesh-colored or red to dark brown in color.

There is a continuing need for a novel, simple and reproducible wound healing therapy to improve wound healing and reduce symptoms associated with wound, such as pain and scar formation, during the wound healing process. Preferably such therapy involves a therapeutic agent that is stable over time, relatively inexpensive to prepare, and achieves its wound healing effects with dose regimens that are associated with minimal toxicity.

BRIEF SUMMARY OF THE INVENTION

It is now discovered that when a glycerophosphate salt is first administered to a wound shortly after the wound was inflicted, the glycerophosphate salt improves wound healing and drastically reduces pain and scar formation.

In one general aspect, an embodiment of the present invention relates to a method of treating a wound in a subject. The method comprises administering to the wound a composition comprising an effective amount of a glycerophosphate salt, wherein the composition is first administered to the wound about 0 to about 7 days after the wound is inflicted.

In another general aspect, an embodiment of the present invention relates to a kit for treating a wound in a subject. The kit comprises:

(1) a composition comprising an effective amount of glycerophosphate salt; and (2) instructions for administering the composition to a wound, wherein the instructions describe first administering the composition to the wound about 0 to about 7 days after the wound is inflicted.

In a preferred embodiment, the kit comprises a bandage impregnated with an effective amount of calcium glycerophosphate (CGP).

In another general aspect, an embodiment of the present invention relates to a multi-purpose wound healing composition. The composition comprises an effective amount of a glycerophosphate salt, and one or more selected from the group consisting of an antiseptic, an immediate local anesthetic, and a longer term analgesic.

In another general aspect, an embodiment of the present invention relates to a method of reducing a scar, comprising: (1) excising a scar tissue to create a new wound; and (2) applying to the new wound a composition comprising an effective amount of a glycerophosphate salt, wherein the composition is first administered to the new wound about 0 to about 7 days after the new wound is inflicted.

An embodiment of the present invention further relates to a method of reducing scar formation from a surgical operation, comprising (1) healing a surgical incision resulting from the surgical operation; (2) excising scar tissue resulting from the healing to create a new wound; and (3) applying to the new wound a composition comprising an effective amount of a glycerophosphate salt, wherein the composition is first administered to the new wound about 0 to about 7 days after the new wound is inflicted.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise embodiments shown in the drawings.

FIGS. 2a-2d are black and white photocopies of the color photographs of the knees of another human subject. He received simultaneous bilateral total knee replacements. His right leg (on the left side of the photographs) was treated with 7.5% (w/w) calcium glycerophosphate (CGP) approximately 70 hours post operation. His left leg (on the right side of the photographs) received no CGP treatment. He received further daily CGP treatments to his right leg and the sequence of photographs shows the results.

FIGS. 3a-3f are black and white photocopies of the color photographs of the nose of a human subject who received bilateral surgical nose excisions followed by the topical treatment of Cellerity® (7.5% (w/w) CGP) to the left-side surgical wound (on the right side of the photographs) 24 hours post surgery and twice daily: FIG. 3a shows the nose on the day of the surgery.

FIGS. 4a-4f are black and white photocopies of the color photographs of the burn wound to the inner forearm of a human subject who received the topical treatment of CGP only to the right-side of the wound (on the left side of the photographs) 24 hours post wound infliction and twice daily: FIG. 4a shows the wound 24 hours post infliction; FIG. 4f shows the wound after 16 days of the CGP treatment. Color variations in the background of the photos are an artifact of the time of the day and the location when the pictures were taken.

FIG. 5a-5e are black and white photocopies of the color photographs of the spider bite wound of a human subject who received the topical treatment of CGP (6.75% (w/w)) to the spider bite wound twice daily: FIG. 5e shows a photograph of the wound after 50 days of the CGP treatment taken without flash light.

DETAILED DESCRIPTION OF THE INVENTION

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

As used herein, the term "subject" refers to an animal, preferably a mammal, who/which has been the object of treatment, observation or experiment. Examples of a subject can be a human, a livestock animal (beef and dairy cattle, sheep, poultry, swine, etc.), or a companion animal (dog, cat, horse, etc).

As used herein, the term "wound" refers to trauma to any of the tissues of the body of a subject. An embodiment of the wound is caused by physical means and results in interruption or a breach of continuity of the skin and flesh of the subject. The wound can be caused by various means, such as a surgical incision, an accident, a disease, or an assault, for example, by a weapon such as a gun or knife.

As used herein, the term "pain" refers to an unpleasant sensation associated with actual or potential tissue damage and mediated by specific nerve fibers to the brain where its conscious appreciation can be modified by various factors. Pain can range in intensities from mild, localized discomfort to severe, agony, or indescribable. Pain can be contained to a discrete area, as in a wound, or it can be more diffuse, as in disorders like fibromyalgia, a chronic condition causing pain, stiffness, and tenderness of the muscles, tendons, and joints. Pain can have qualities such as stinging, sharp, throbbing, dull, nauseating, heat sensation, burning and shooting. Pain includes both spontaneous pain and chronic pain.

Pain can have a wide variety of causes, including, but not limited to, inflammation, injury, disease, muscle spasm and the onset of a neuropathic event or syndrome. Pain can be experienced when bodily tissues are subjected to mechanical, thermal or chemical stimuli of sufficient intensity to be capable of producing tissue damage. Pain can resolve when the stimulus is removed or the injured tissue heals. However, under conditions of inflammatory sensitization or damage to actual nerve tissue, pain can become chronic or permanent despite apparent tissue healing. Pain experienced due to stimuli can become disproportionately intense and persistent. Pain can be felt in the absence of an external stimulus. Examples of pain include inflammatory pain and neuropathic pain.

As used herein, the term "bandage" refers to a piece of cloth or other material, of varying shape and size, used to be applied to a body part to provide compression, protect from external contamination, prevent drying, absorb drainage, prevent motion, promote healing or prevent further harm, or retain surgical dressings. As used herein, the term "bandage" include a plaster bandage, dressing, and a piece of material used to support or hold in place a dressing or provide support to the body on its won. Bandages are available in a wide range of types, from generic cloth strips, to specially shaped bandages designed for a specific limb or part of the body.

As used herein, the term "antiseptic" refers to an antimicrobial substance that can be applied to a tissue or the body of a subject to reduce the possibility of infection, sepsis or putrefaction. An "antiseptic" can be a germicide that kills or destroys a microbe, such as an antibiotic that kills bacteria. An "antiseptic" can also be a microbiostatic agent that only prevents or inhibits the growth of a microbe, such as a bacteriostatic that prevents the growth of bacteria.

The term "effective amount" as used herein means that amount of a glycerophosphate salt that accelerates the healing of a wound and/or reduces a symptom related to the wound, such as pain or scar formation, in a subject as compared to an otherwise identical treatment without the effective amount of glycerophosphate salt.

In one embodiment of the invention, an effective amount of a glycerophosphate salt accelerates the healing of the wound in a subject, such that it takes about 90%, 80%, 70%, 60%, 50%, 40%, 30%, 20%, 10% or less, preferably about 30-50%, of the time that would have taken to heal the wound had the subject not received an effective amount of the glycerophosphate salt.

In another embodiment of the invention, of even greater importance than the enhanced chronology of the wound healing process, the application of an effective amount of glycerophosphate salt to a wound of a subject results in a clinically observable beneficial effect in the reduction of scar formation such that the resulting scar is about 90%, 80%, 70%, 60%, 50%, 40%, 30%, 20%, 10% or less, of the scar that would have resulted from the wound had the subject not received an effective amount of the glycerophosphate salt.

In another embodiment of the invention, the application of an effective amount of glycerophosphate salt to a wound of a subject results in a clinically observable beneficial effect in the reduction of pain or another symptom, such that the pain or the other symptom related to the wound is reduced to about 90%, 80%, 70%, 60%, 50%, 40%, 30%, 20%, 10% or less, of the pain or the other symptom that would have resulted from the wound had the subject not received an effective amount of the glycerophosphate salt.

Standard procedures can be performed to evaluate the effect of the administration of a glycerophosphate salt to a subject, thus allowing a skilled artisan to determine the effective amount of the glycerophosphate salt to be administered to the subject. For example, the clinically observable beneficial effect in scar reduction can be observed by directly viewing the wound or by indirectly viewing photographs of the wound. The beneficial effect can be a reduction, substantially obliteration, or complete interdiction of the "hash marks" resulting from the surgical closure staples subsequent to removal of the staples. In addition, various animal models of pain, such as the neuroinflammation models (Chacur et al., Pain 94:231-44 (2001); Milligan et al., Brain Res 861: 105-16 (2000)), and acute nociceptive test models, can be used to determine the effective amount of the compound for reducing pain.

The clinically observable beneficial effect can be a situation that symptoms related to a wound are prevented from further development or aggravation, or develop to a lesser degree than without administration of the composition of the present invention, when a composition of the present invention is administered to a subject after the symptoms are observable. The clinically observable beneficial effect can also be a situation in which symptoms related to a wound are prevented from occurring or subsequently occur to a lesser degree than without administration of the composition of the present invention, when a composition of the present invention is administered to a subject before the symptoms are observable.

One skilled in the art will recognize that the "effective amount" of a glycerophosphate salt to be used in the instant invention can vary with factors, such as the particular subject, e.g., age, diet, health, etc., size of the wound, severity and complications of the wound sought to be treated, the mode of administration of a glycerophosphate salt, the particular glycerophosphate salt used, the time when the glycerophosphate salt is first applied to the wound, etc. Standard procedures can be performed to evaluate the effect of the administration of a glycerophosphate salt to a wound, thus allowing a skilled artisan to determine the effective amount of the glycerophosphate salt to be administered to the wound in view of the present disclosure.

The effective amount of a glycerophosphate salt per administration can be, for example, about 0.1 gram to about 3.0 grams, and preferably about 0.3 gram to about 1.0 gram. The preferred daily dosage of a glycerophosphate salt can be about 0.6 gram to about 18 grams, and more preferably about 1.8 grams to about 6 grams. However, the number of doses per day and the quantity of the glycerophosphate salt which may be administered to a subject can be virtually unlimited.

As used herein, the term "glycerophosphate salt" refers to a chemical compound that is derived from glycerophosphate, in which one or more of the hydrogens of the phosphate group of glycerophosphate are replaced by a basic radical, in particular embodiments by a metal ion. As used herein, the term "glycerophosphate" refers to an anion of a phosphoric ester of glycerol, in which a carbon atom of glycerol bonds to an oxygen atom in the phosphate group of phosphoric acid. A glycerophosphate salt can be a chiral molecule, i.e., it can exist in two forms that are nonsuperimposable mirror images. It is intended that the present invention includes within its scope the stereochemically pure isomeric forms of a glycerophosphate salt and/or their racemates.

In particular embodiments, methods of the invention utilize one or more glycerophosphate salts selected from the group consisting of calcium glycerophosphate (CGP), magnesium glycerophosphate, zinc glycerophosphate, manganese glycerophosphate, lithium glycerophosphate, cupric glycerophosphate, ferric glycerophosphate, quinine glycerophosphate, glycerophosphate disodium, glycerophosphate dipotassium, glycerophosphate barium, and glycerophosphate strontium.

The effective amount of a glycerophosphate salt takes into account of the efficacy of the particular glycerophosphate salt used. For example, extreme caution is taken to use lithium glycerophosphate in a method according to an embodiment of the present invention, because its effects on mood and its possible adverse effects on cardiac and renal function. The effective amount also takes into account of other properties of the glycerophosphate salt, such as toxicity (e.g., cupric glycerophosphate).

In a preferred embodiment, the invention relates to calcium glycerophosphate. As used herein, the term "calcium glycerophosphate" or "CGP," also known as "glycerophosphate calcium," refers to a chemical compound having a molecular formula of $C_3H_7CaO_6P$ in its anhydrous form. "CGP" can also exist as a hydrate, including the monohydrate and the dihydrate. Examples of calcium glycerophosphate include, but are not limited to, any one, or any combination of two or more of the three isomers of CGP, namely β-glycerophosphoric acid calcium salt (($HOCH_2$)$_2CHOPO_3Ca$) and D(+) and L(−)-α-glycerophosphoric acid calcium salt ($HOCH_2CH(OH)CH_2OPO_3Ca$).

Calcium glycerophosphate available from various commercial sources can be used in the present invention. In one embodiment, Cellerity®, a topical lotion available from AkPharma Inc. (Pleasantville, N.J. 08232), can be used in the present invention. Other commercially available CGP also includes CGP available from Astha Laboratories Pvt, Ltd, B-4, Industrial Estate, Sanathnagar, Hyderabad-18, India, and Seppic Inc., 30 Two Bridges Road, Fairfield, N.J.

In another embodiment, the invention utilizes a glycerophosphate salt other than calcium glycerophosphate. Calcium glycerophosphate may be contraindicated for persons with poor renal function or who are in renal failure. The presence of calcium ion may also suppress activities of certain drugs, e.g., certain antibiotic drugs, that are co-administered with the glycerophosphate salt. Therefore, methods of the invention also utilize one or more glycerophosphate salts selected from the group consisting a Na, K, Mg, or Sr salt of glycerophosphate, or any other non-calcium glycerophosphate salts described herein.

As used herein, the term "instructions" when used in the context of a kit includes a publication, a recording, a diagram or any other medium of expression which can be used to communicate the usefulness of the kit for its designated use. The instructions may, for example, be affixed to or included within a container for the kit.

Embodiments of the present invention comprise a method, a composition and a kit for treatment of wounds, whether the wounds resulting from battlefields, accidents, surgeries or chronic diseases. Embodiments of the present invention provide "all in one" wound treatment methods and compositions that are so effective that they can be used as a first option for the treatment of all types of wounds, whether said treatment be provided by battlefield medic, municipal emergency responder, operating room surgeon, clinical practitioner or by the sufferer him/herself.

Figure 1A:
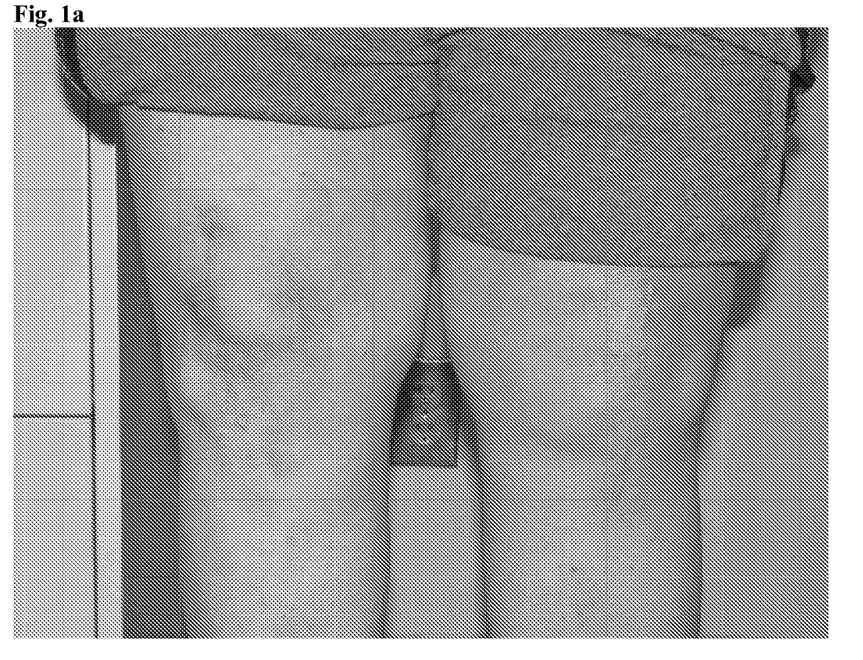
FIGS. 1a and 1b are black and white photocopies of the color photographs of the knees of a human subject. Her right leg (on the left side of the photographs) received a total knee replacement and was treated with 7.5% by weight (w/w) calcium glycerophosphate 10 weeks post operation (FIG. 1a). Her left leg (on the right side of the photographs) received a total knee replacement and was treated with 7.5% (w/w) calcium glycerophosphate 48 hrs post operation (FIG. 1b). The total knee replacement on her right leg was performed more than 5 months before the total knee replacement on her left leg.
Figure 1B:
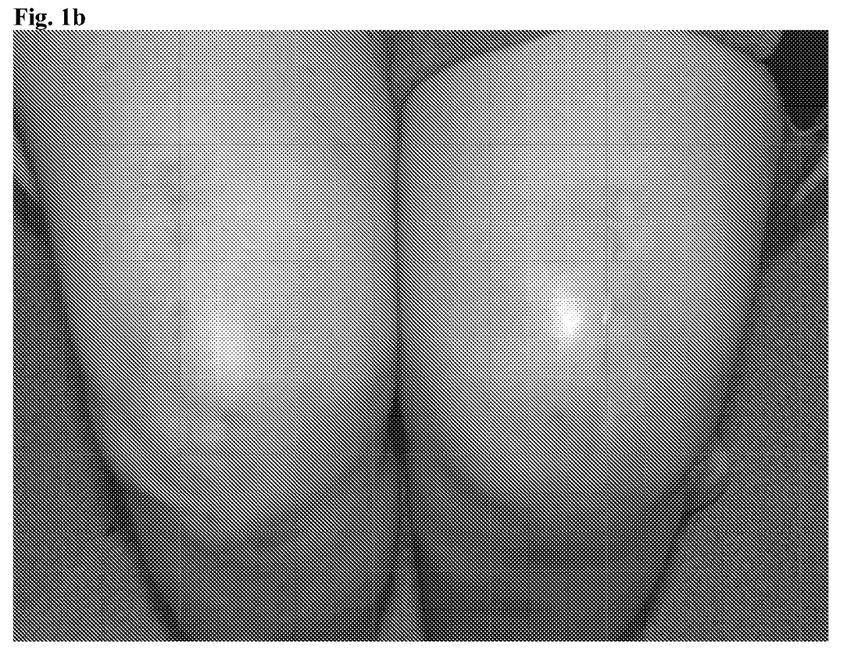

It is discovered in the present invention that when a glycerophosphate salt is first administered to a wound shortly after the wound was inflicted, the administration significantly improved wound healing and drastically reduced symptoms associated with the wound, such as pain and scar formation. A glycerophosphate salt provided some advantages in would healing and scar reduction even when the glycerophosphate salt was first administered to the wound 12 days after the wound was inflicted (data not shown). However, a more drastic improvement in wound healing and scar reduction was observed when the glycerophosphate salt was first administered to a wound 48 hours after the wound was inflicted (FIGS. 1a and 1b).

Accordingly, in one general aspect, the present invention relates to a method of treating a wound in a subject. The method comprises administering to the wound a composition comprising an effective amount of a glycerophosphate salt, wherein the composition is first administered to the wound about 0 to about 7 days after the wound is inflicted.

In embodiments of the present invention, the composition is first administered to the wound about 0 hour to about 6 days, about 0 to about 5 days, about 0 to about 4 days, about 0 to about 3 days, about 0 to about 2 days, about 0 to about 1 day, or about 1 to about 12 hours after the wound is inflicted. Most preferably, the composition is administered immediately, e.g., 0 to 3 hours, after the wound is inflicted. The wound can be inflicted by various means, such as a surgery, an accident, an assault, or a disease.

In embodiments of the present invention, the administered composition is a multi-purpose wound composition that comprises one or more additional ingredients selected from the group consisting of an antiseptic, an immediate local anesthetic, and a longer term anesthetic. Each single administration of the composition performs at least two essential tasks on a wound including, but not limited to, (1) stanching or reducing bleeding from the wound, e.g., by sealing the wound and expediting the clotting process, (2) absorbing or soaking up exudate from the wound, such as blood, plasma and other fluids extruded from the wound, containing the exudate in one place, (3) providing antisepsis and protecting the wound from infections, (4) providing immediate localized pain relief, (5) providing longer term localized pain relief, (6) engendering more rapid healing of the wound, (7) reducing eventual scarring, and (8) providing greater epidermal flexibility in wound areas where skin flexure is essential, e.g., knee, elbow, etc.

The composition can be administered to the wound in any form suitable for administration to a wound, such as in a form of dry powder, granule, wet paste, flowing liquid, dry or wet spray, embodying such thickeners, stabilizers and/or emulsifiers as may be deemed appropriate or necessary to assure desired suspension uniformity. All the above can be used for a number of applications, including, but not limited to, direct application to skin, application to overlying bandage, or embedded in 'strip and apply' bandage from the factory.

The composition may also contain an admixed substance that when moistened or otherwise actuated, either throughout the composition on a time-effect basis, or via application to the outer surfaces of same for immediate effect, will stiffen or harden the composition so that such composition will now assume a body-molded hemostatic form and will thereby be more effective as a single hemostatic, wound protective unit, for example, forming an ad hoc wound cast.

In one embodiment of the present invention, an effective amount of a glycerophosphate salt, in a form of dry powder, granules, or gel is applied directly to the wound via spray, physical transfer by finger or implement to form a coating on the wound. The coating can contain a final local concentration of the glycerophosphate salt of about 0.5%-100% by weight. For example, the final local concentration of the glycerophosphate salt can be about 0.5% to about 5%, about 5% to about 15%, about 15% to about 25%, about 25% to about 35%, about 35% to about 45%, about 45% to about 55%, about 55% to about 65%, about 65% to about 75%, about 75% to about 85%, or about 85% to about 100%, by weight. It has been adequately observed on epidermal skin that lower concentrations of CGP, such as between 1% and 2% by weight, favorably affect apparent rhino mucosal passage inflammation, thus are effective for wound healing.

When the composition is applied as dry powder, for example, to stanch or reduce bleeding from a wound, or to absorb or soak up exudate from the wound, the concentration of the glycerophosphate salt is preferably 30% or more by weight (w/w) in the composition, although lower concentrations of the glycerophosphate salt can also be applied.

In another embodiment, an effective amount of a glycerophosphate salt is applied to the wound by rinsing the wound with a solution or suspension containing about 0.5% to about 75% by weight of the glycerophosphate salt. For example, the solution or suspension can contain about 0.5% to about 5%, about 5% to about 15%, about 15% to about 25%, about 25% to about 35%, about 35% to about 45%, about 45% to about 55%, about 55% to about 65%, or about 65% to about 75%, by weight of the glycerophosphate salt.

In another embodiment of the present invention, the composition is administered by the indirect application of a bandage over the wound. The bandage comprises the composition according to embodiments of the invention. The bandage can be any type of bandages that are useful for wound treatment. Compositions of the present invention can be impregnated or made part of the bandages using methods known in the art in view of the present disclosure.

In one embodiment of the present invention, the bandage is a plaster bandage that is impregnated with plaster, applied moist and a composition according to an embodiment of the invention. The plaster bandage can be used to make a rigid dressing for a wound associated with a fracture or diseased joint.

In another embodiment of the present invention, the bandage is an adhesive bandage that comprises an adhesive cover and a non-adhesive absorbent pad. The adhesive cover can be woven fabric, plastic, or latex rubber which has an adhesive. The non-adhesive absorbent pad can be impregnated with a composition according to an embodiment of the invention. The adhesive bandage is applied to small, not serious wound, such that the absorbent pad covers the wound (but does not stick to the wound), and the adhesive cover sticks to the surrounding skin to hold the pad in place and prevent dirt from entering the wound.

In yet another embodiment of the present invention, the bandage is a dressing, such as a surgical dressing that is impregnated with a composition according to an embodiment of the invention, or a gauze, i.e., a thin, translucent fabric with a loose open weave. A dressing can be made of any suitable materials, such as cloth, gauzes, films, gels, foams, hydrocolloids, alginates, hydrogels and polysaccharide pastes, granules and beads. Preferably, the dressing should control the moisture content, so that the wound stays moist; protect the wound from infection; remove slough; and maintain the optimum pH and temperature to encourage healing. The dressing is preferably sterilized and kept in sterile condition, e.g., wrapped in stile wrapping, prior to use. However, dressings can also be improvised as needed to fulfill some basic functions of a dressing, e.g., stanching bleeding and, absorbing exudate.

Also included in the present invention is an adhesive tape described in the PCT Application No. PCT/US08/64516, the contents of which are incorporated herein by reference.

How often and how long a glycerophosphate salt is administered to a subject depends on the type of treatment or prevention, how the subject responds to the glycerophosphate salt, factors associated with the subject, e.g., age, diet, health, etc., the size of the oral lesion, ability to tolerate the glycerophosphate salt, and the types of glycerophosphate salt used. A glycerophosphate salt can be administered on a regimen of one to multiple times per day. Preferably, a glycerophosphate salt is administered to the subject at intervals during the day, such as after breakfast, lunch, dinner, and upon retiring. In one embodiment, a composition containing glycerophosphate salt is administered at least once daily, where "daily" and "days" mean a 24-hour period. The composition can be applied once or multiple times daily until the wound is completely healed or desirable results for scar reduction or pain relieving are achieved. The composition can be applied for 30 or more consecutive days, alternatively for 14 or more consecutive days, alternatively for 7 or more consecutive days and alternatively for 2 or more consecutive days.

In embodiments of the present invention, the composition administered to the wound comprises a glycerophosphate salt selected from the group consisting of calcium glycerophosphate, magnesium glycerophosphate, zinc glycerophosphate, manganese glycerophosphate, lithium glycerophosphate, cupric glycerophosphate, ferric glycerophosphate, quinine glycerophosphate, glycerophosphate disodium, glycerophosphate dipotassium, glycerophosphate barium, glycerophosphate strontium, and combinations thereof.

In a preferred embodiment, the administered glycerophosphate salt is calcium glycerophosphate. In a more preferred embodiment, the method comprises administering to the wound a multi-purpose wound healing composition A-FORT™, which comprises an effective amount of calcium glycerophosphate (CGP); an antiseptic including, but not limited to, alcohols, quaternary ammonium compounds, chlorhexidines, iodophors, triclosan 2%, boric acid, hydrogen peroxide, octenidine dihydrochloride, phenol (carbolic acid) compounds and sodium chloride; an immediate local anesthetic including, but not limited to, benzocaine, lidocaine, amino esters such as benzocaine, chloroprocaine, cocaine, cyclomethycaine, dimethocaine/larocaine, propoxycaine, procaine/novocaine, proparacaine or tetracaine/amethocaine, amino amides such as articaine, bupivacaine, carticaine, cinchocaine/dibucaine, etidocaine, levobupivacaine, lidocaine/lignocaine, mepivacaine, piperocaine, prilocaine, ropivacaine or trimecaine, a combination thereof, such as lidocaine/prilocaine (emla); and natural local anesthetics including, but not limited to, saxitoxin or tetrodotoxin; and a long term analgesic, including, but not limited to, capsaicin, rubefacients, NSAIDs, benzydamine, mucopolysaccharide polysulphate and salicylamide.

A-FORT™ in any of the suitable forms can be applied to a wound in a whole array of options. For example, in first aid situations, A-FORT™ dry powder can be first sprinkled on wound followed by bandaging; A-FORT™ paste can be applied to a wound directly from a dispensing tube followed by bandaging; A-FORT™ can be sprayed to a wound either wet or dry followed by bandaging; A-FORT™ can be applied to the wound in any form, followed by winding gauze or other absorptive bandage at a single time, then A-FORT™ can be applied again as the first layer of an absorptive bandage, followed by winding and repeat of the process up to several times if deemed necessary.

In the clinic or operating room, the more settled environment would permit the same choices to post-surgery wounds, from surface epidermal layer loss to sutured operation incision. The glycerophosphate salt, such as CGP, can be applied by itself to a wound with no other addition, and the wound will still receive the first to the fourth benefits discussed above. The glycerophosphate salt can also be applied in combination with other agents, such as those an antiseptic, an immediate local anesthetic, and a longer term anesthetic. The actual percentages of each agent to be applied to the wound are based on specific added combinants and their potencies. The glycerophosphate salt, alone or in combination with other active ingredients, can be applied directly to the wound or as embedded in bandages such as surgical dressings, gauze, Ace Bandages, etc., promptly after the surgery.

The method of the present invention can be combined with one or more additional methods of wound treatment. In particular embodiments, the method of the present invention can be combined with one or more additional methods for minimizing scars. Such additional methods include, but are not limited to, topical treatment, e.g., by silicone sheets; surgical excision; steroid injections; pressure therapy; laser and cryotherapy treatments; and chemical peels, etc.

In one embodiment, a method of the present invention can be combined with a method of surgical excision of a scar. The method comprises: (1) excising a scar tissue to create a new wound; and (2) applying to the new wound a composition comprising an effective amount of a glycerophosphate salt, wherein the composition is first administered to the new wound about 0 to about 7 days after the new wound is inflicted. Preferably, the method further comprises stitching up or fastening the new wound.

Given the unique nature of glycerophosphate salt, such as CGP, to induce epidermal tissue to heal and bond, it would be entirely within the realm of practicality, to envision a two-stage operation to reduce scar formation after an operation, preferably a major operation. An exemplary two-stage operation includes: (1) healing a surgical incision resulting from an operation; (2) excising scar tissue resulting from the healing, preferably, after an appropriate time, e.g., from 6 months to 2 years after the original operation, to create a new wound; and (3) applying to the new wound a composition comprising an effective amount of a glycerophosphate salt, wherein the composition is first administered to the new wound about 0 to about 7 days after the new wound is inflicted.

The methods can be applied to reduce or erase scars from any surgical operation or any therapeutic or cosmetic scar revision surgery. In a preferred embodiment, the surgical operation is a major operation, such as a knee replacement operation.

Many methods can be used to heal the original surgical incision from the major operation. In a preferred embodiment, a composition comprising an effective amount of a glycerophosphate salt is administered to the surgical incision. Preferably, the first administration of the glycerophosphate salt occurs about 0 to about 7 days after the original operation, most preferably within 72 hours.

The second stage of the operation is performed, preferably when the original surgical incision has fully or substantially healed, which can take 6 months to 2 years post the original operation. At such time, the scar resulting from the healing of the staple-forced join of the original deep surgical incision has left as residue, considerable obtrusive fibroblastic or keloid tissue, which extrudes and/or curls some skin and fibroblastic tissue permanently. A cut, such as a "v" shape cut or any other shape cut, by a cosmetic surgeon is made to excise all fibroblastic/keloid tissue. The new, shallow wound, can be pulled and fastened together utilizing an appropriate method of fastening, such as standard surgical stitching, including, but not limited to, skin stitching, subcuticular zigzag closure, utilizing a soluble stitching material, e.g., "Vicryl*", or other means acceptable to the surgeon. Epidermal skin edges are pulled to perfect abutment or slight overlap, as suits the cosmetic or reparative surgeon's common practice and/or best judgment and held in place by any appropriate method of fastening such as those described above. A composition comprising an effective amount of a glycerophosphate salt is administered to the new wound, promptly and continuously two or more times per day until the new wound is healed, which may take about 10 days. Preferably, the first administration of the glycerophosphate salt occurs about 0 to about 7 days after the new wound is inflicted.

The above methods have every realistic likelihood of reducing, revising, removing or erasing old scars, whether several months or several years after the scar was formed. Note that this "old scar revision/erasure" method in fact constitutes de novo surgery and operates under the same principles stated elsewhere in this patent application.

In another particular embodiment, the method of the present invention can be combined with one or more additional methods for reducing pain. In embodiments of the present invention, a glycerophosphate salt can be administered in combination with one or more additional analgesics, including, but not limited to, a second glycerophosphate salt; morphine or other opiate receptor agonists; nalbuphine or other mixed opioid agonist/antagonists; tramadol; baclofen; clonidine or other alpha-2 adrenoreceptor agonists; amitriptyline or other tricyclic antidepressants; gabapentin or pregabalin, carbamazepine, phenytoin, lamotrigine, or other anticonvulsants; and/or lidocaine, tocainide, or other local anesthetics/antiarrhythmics.

In another particular embodiment, the method of the present invention can be combined with one or more additional methods for reducing inflammation. In embodiments of the present invention, a glycerophosphate salt can be administered in combination with one or more anti-inflammation agents including, but not limited to: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC$_\gamma$ isoform inhibitors (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including mu-opioid, delta-opioid, and kappa-opioid receptor subtype agonists; (13) purinoceptor agonists and antagonists including P$_{2X}$ receptor antagonists and P$_{2Y}$ receptor agonists; and (14) adenosine triphosphate (ATP)-sensitive potassium channel openers.

In other particular embodiments of the present invention, a glycerophosphate salt can be administered in combination with one or more anti-inflammation agents that also act as anti-spasm agents. Suitable anti-inflammatory agents that also act as anti-spasm agents include serotonin receptor antagonists, tachykinin receptor antagonists, ATP-sensitive potassium channel openers and calcium channel antagonists. Other agents that may be utilized in the combination specifically for their anti-spasm properties including endothelin receptor antagonists, calcium channel antagonists and the nitric oxide donors (enzyme activators).

The method of the present invention can be used to treat wound in any subject. In a preferred embodiment, the subject is a human subject. In another preferred embodiment, the subject is a domestic animal, such as a pet.

Another general aspect of the present invention is a kit for treating a wound in a subject. The kit comprises: (1) a composition comprising an effective amount of glycerophosphate salt; and (2) instructions for administering the composition to a subject having a wound, wherein the instructions describe first administering the composition to the wound about 0 to about 7 days after the wound is inflicted.

Any of the compositions according to embodiments of the present invention can be included in the kit. The composition can comprise a glycerophosphate salt as the only active ingredient. The composition can also comprise a combination of a glycerophosphate salt and one or more additional active ingredients selected from the group consisting of an antiseptic, an immediate local anesthetic, and a longer term analgesic.

In one embodiment, the kit comprises a bandage that is impregnated with an effective amount of glycerophosphate salt, preferably CGP.

In a preferred embodiment, the kit is a First Aid kit that can be used to provide initial and/or immediate care for a wound. In a more preferred embodiment, the First Aid kit comprises A-FORT™ in any of the described forms.

In another general aspect, the present invention relates to a multi-purpose wound-healing composition that can be used for methods of treating a wound in a subject. The composition comprises an effective amount of a glycerophosphate salt and one or more additional ingredients selected from the group consisting of an antiseptic, an immediate local anesthetic, and a longer term anesthetic.

In a particular embodiment, the multi-purpose wound healing composition comprises an effective amount of glycerophosphate salt selected from the group consisting of calcium glycerophosphate, magnesium glycerophosphate, zinc glycerophosphate, manganese glycerophosphate, lithium glycerophosphate, cupric glycerophosphate, ferric glycerophosphate, quinine glycerophosphate, glycerophosphate disodium, glycerophosphate dipotassium, glycerophosphate barium, glycerophosphate strontium, and combinations thereof, and at least one of the following components:

(1) one or more antiseptics to reduce the possibility of infection, sepsis, or putrefaction, which can be selected from any of a range of possible antiseptics that are suitable for application to wounds, including but not limited to, alcohols (such as ethanol, 1-propanol, isopropanol, or mixtures thereof); iodine (such as tincture of iodine, povidone-iodine); cationic surfactants (such as benzalkonium chloride, chlorhexidine or octenidine dihydrochloride); quaternary ammonium compounds (such as benzalkonium chloride (BAC), cetyl trimethylammonium bromide (CTMB), cetylpyridinium chloride (Cetrim, CPC) and benzethonium chloride (BZT)); anionic surfactants (such as soaps); boric acid; hydrogen peroxide; 2-phenoxyethanol; phenol; sodium chloride and sodium hypochlorite, or combinations thereof;

(2) one or more immediate local anesthetics to assist in instant pain relief, which can be selected from any of a range of possible local anesthetics that are suitable for application to wounds, including but not limited to, benzocaine, lidocaine, prilocaine, bupivicaine, levobupivacaine, ropivacaine, dibucaine, tetracaine/amethocaine, chloroprocaine, cocaine, cyclomethycaine, dimethocaine/larocaine, propoxycaine, procaine/novocaine, proparacaine, articaine, carticaine, etidocaine, mepivacaine, piperocaine, trimecaine, or combinations thereof; and (3) a longer term analgesics or anesthetic to assist in longer term pain relief, which can be selected from any of a range of possible longer term analgesics that are suitable for application to wounds, including but not limited to, capsaicin, ibuprofen, diclofenac.

In an embodiment of the present invention, when an alcohol or alcoholic compound is utilized, the alcohol or alcoholic compound is preferably used sequentially with the glycerophosphate salt, e.g., it is applied to the wound first and allowed to dry before the application of the glycerophosphate salt. The glycerophosphate salt, such as CGP, is insoluble in alcohol and it will have the potential to bead off on the wound surface.

In another embodiment of the present invention, when an alcohol or alcoholic compound is utilized, it may be combined with a glycerophosphate salt, such as CGP, in a suspension and applied to the wound in a single antiseptic application. Preferably the suspension is well shaken before the application. The composition may contain additional ingredient of a stabilizer, e.g., sodium carboxymethylcellulose gum, guar gum, carrageenan or other, used to thicken the composition. When utilized at the levels of 0.25% to 5% (w/w), preferably 0.5% to 3% (w/w), the stabilizer can produce a desirably consistency of the product for such application as a lotion.

In one embodiment of the present invention, the composition can comprise one or more other agents that are useful for wound healing, and/or reduction of symptoms related to wound, such as pain and scar formation. The multi-purpose wound healing composition can be formulated in various forms that are suitable for application to wounds using methods know in the art in view of the present disclosure. For example, the composition can be formulated in a form of dry powder, granules, gel, liquid solution or suspension, that can be applied to the wound directly. The composition can also be impregnated or made part of a bandage, which indirectly applies the composition to a wound when the bandage is used to overlay the wound.

Compositions useful in the present invention can be formulated using any method known to those skilled in the art in view of the present disclosure. To prepare the compositions for administration to a subject, one or more glycerophosphate salts, optionally other active ingredients, are intimately admixed with an acceptable carrier according to conventional pharmaceutical compounding techniques. The composition can contain about 0.1 mg to about 3000 mg of a glycerophosphate salt, and can be constituted into any form suitable for the mode of administration selected. Carriers include one or more excipients such as binders, suspending agents, lubricants, flavorants, sweeteners, preservatives, dyes, and coatings. Carriers can take a wide variety of forms depending on the form of preparation desired for administration. For parenterals, the carriers usually comprise sterile water, though other ingredients, for example, for purposes such as aiding solubility or for preservation, can also be included. For injectable suspensions, appropriate liquid carriers, suspending agents and the like can be employed. For liquid oral preparations, for example, suspensions, elixirs and solutions, suitable carriers and additives include water, glycols, oils, alcohols, flavoring agents, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For topical compositions, such as cream or gel, suitable carriers and additives include, for example, thickeners, humectants, keratolytics, oils, emollients, surfactants, preservatives, colorants, UV blockers, antioxidants, perfumes, mineral oil, liquid petrolatum, white petrolatum, glycerin, polyethylene glycol and propylene glycol.

The compositions for administration herein can contain, per dosage unit, e.g., tablet, capsule, powder, injection, teaspoonful and the like, an amount of the active ingredient necessary to deliver an effective amount as described above. A glycerophosphate salt can be formulated in an extended release form suitable for once-weekly or once-monthly administration. Methods are known to those skilled in the art to manufacture the extended release dosage form.

Compositions of the present invention can be formulated at various pH levels would be suitable for purposes of the invention in view of the present disclosure. In preferred embodiments, compositions useful for the present invention have a pH of about 4.4 to about 8.4, more preferably, at a pH of about 5.45 to about 7.0.

Compositions for administration herein can be administered in many forms, such as solutions, suspensions, tablets, pills, capsules, spray, gels, drops, sustained release formulations, powders or active ingredient impregnated bandages.

In a particular embodiment of the invention, compositions for administration herein are administered to a subject topically. Creams, gels, ointments, powders, aerosols and solutions are suitable for topical administration. Preferably, the compositions are dermatologically acceptable and do not cause significant skin irritation under normal usage circumstances with typical patients when the compositions are applied to the skin. Compositions containing a glycerophosphate salt suitable for topical administration have been described, for example, in US2004037766 and U.S. Pat. No. 5,972,321, which are incorporated herein by references.

In one embodiment for topical administration, the composition for administration comprises one or more glycerophosphate salts, a solvent, and at least one excipient selected from thickeners, humectants, keratolytics, oils, emollients, surfactants, preservatives, colorants, UV blockers, antioxidants, perfumes, mineral oil, liquid petrolatum, white petrolatum, glycerin, polyethylene glycol and propylene glycol. A thickener can be any agent useful as an aid to thicken or add structure to a topical formulation, or to result in a viscosity suitable for dermatologic applications. Non-limiting examples of thickening agents are gums and natural polysaccharides, mineral thickeners, oils, and synthetic polymeric thickeners.

In another embodiment for topical administration, the composition for administration comprises one or more solvents in an amount of about 10% to about 90% by weight, one or more glycerophosphate salts in a total amount of about 0.001% to about 25% by weight, a polymeric thickener in an amount of about 0.05% to about 5% by weight, and one or more keratolytic agents are present in a total keratolytic agent concentration amount of about 0.015% to about 25% by weight. The solvent is preferably nonalcoholic. The polymeric thickener can be a polyacrylic acid thickener or an alkylhydroxycellulose thickener. The keratolytic agent can be selected from the group consisting of alpha- and beta-hydroxycarboxylic, beta-ketocarboxylic acids, a salicylate, and salts, amides or esters thereof.

In yet another embodiment for topical administration, the composition for administration further contains a preservative. Preferably the preservative is food grade or pharmaceutical grade. Examples of preservatives that can be used in the composition include, but are not limited to, methylparaben, ethylparaben, butylparaben, propylparaben, and any other preservative that is typically used in water-based cosmetics, such as creams and lotions and some bath products. The preservative is present at an amount that is sufficient to prevent the composition from supporting the growth of microbes such as bacteria, fungi, or yeasts.

The present invention delivers an array of advantages. The application of a composition of the present invention, such as A-FORT™, to a wound, will in each application achieve multiple beneficial effects, such as to help to stop bleeding, provide wound antisepsis, help to repair the wound, palliate pain both immediate and in the days thereafter, enhance longer term healing and minimize scarring, in addition to other recognized or unrecognized benefits.

While not wishing to be bound by theory, it is believed that some of the advantages are at least due to the following reasons.

First, CGP is only sparingly soluble in water. Thus, when CGP is applied to a blood-flowing wound and held there by mechanical means, i.e., bandaging, it will not dissolve in blood but will cake up and form a dam, assisting in the stanching of bleeding.

Second, calcium ion is itself an essential component in the wound-area blood clotting (hemostatic) mechanism. For example, fibrin clot formation is correlated with higher levels of free ionized calcium (iCa) (Gieseler et al., *Thromb Haemost.* 2007 June; 97(6):1023-30); several serine protease coagulation factors are activated in a highly $Ca^{++}$ dependent manner. Application of calcium ion to the wound may be advantageous over extrinsical application of coagulation factors, such as Factor VII, and is vastly less expensive. Calcium ion is also superior in certain respects to other available hemostats, e.g., chitin ("Chitosan®"), which has a somewhat mixed record in terms of effectiveness, and to mineral zeolite ("Quikclot®"), which, while hemostatically effective, has serious issues in terms of patient pain in that it imparts thermal heat sufficient to damage tissue, in some cases, giving it "an unacceptable risk:benefit ratio in non-battlefield conditions" and limiting its military use. Further, neither of the above is demonstrated in having further beneficial effects on the wound beyond the urgent immediate trauma event time framework; see for example, Alam et al., *Military Medicine,* 2005, 170:1:63.

Third, CGP is an acid-binding substance with a natural pH of about 8.4 and is a known acid reducing agent over a wide range of uses. Serosanguinous wounds go naturally acidic, for body protective reasons. For this reason, the presence of CGP on/in a wound will bind and neutralize the naturally forming acid in a bloody wound surface, thereby reducing or removing that pain-inducing source from the exposed nerve endings at the wound site. This localized relief may in turn reduce or obviate the need for administration of systemic narcotic pain relievers to a seriously wounded subject being treated at an accident site or in an emergency room, when such subject may already be in shock or be otherwise ill advised to be the recipient of a further central nervous system depressant.

Fourth, the calcium ion and the glycerophosphate ion are demonstrated to be of importance in cellular repair and repair of tissue damage via a number of mechanisms explained in literature and patents granted and pending, see for example, US20040037766. Greater response of epithelial cells to $Ca^{++}$ signals than that of fibroblasts was reported (see, for example, Lansdown, *Wound Repair and Regeneration*, September-October 2002).

Fifth, an antiseptic/antibiotic of any kind, such as "chloroprep" can be used together with CGP, not only as a proper general procedure, but to assure sterility of composition as laid down on the wound and to partially compensate for the loss of the body's protective wound-acid formation.

Sixth, an application of at least one of two types of pain relievers, an immediate local anesthetic and a longer term analgesic, both known for such properties, can also be included. The immediate local anesthetic is a short term, immediate "numbness" provider, e.g., benzocaine, lidocaine, etc. It helps not only to stop immediate pain, when teamed with the acid-neutralizing CGP, but also to numb the site to the immediate effects of the longer term anesthetic, capsaicin. The longer term analgesic or anesthetic, e.g., capsaicin, initially stings when it is first applied to the wound. But it then has a residual pain palliative effect.

This invention will be better understood by reference to the non-limiting example that follows, but those skilled in the art will readily appreciate that the example is only illustrative of the invention.

EXAMPLES

A female human patient received total knee replacement surgeries on her right leg and left leg on Aug. 22, 2007 and Jan. 30, 2008, respectively, from the same doctor with the same surgery procedure. With the doctor's approval, treatment with AkPharma's Cellerity® topical lotion (7.5% (w/w) calcium glycerophosphate formulation, pH 5.65) to her right leg commenced 10 weeks post-operation (post-op) on Nov. 14, 2008, and treatment with AkPharma's Cellerity® topical lotion (7.5% (w/w) calcium glycerophosphate formulation, pH 5.65) to her left leg commenced 48 hrs post-op. Since the commencement of the treatment, 2 ml of Cellerity® lotion was topically applied to the wounds of the knee surgeries twice daily everyday.

Color photographs of the knees were taken 6 weeks post-op of the left leg. The hash marks from the staples on the lower legs (FIG. 1a) and the embedded ladder-like staple scars on the upper leg (FIG. 1b) were both much more prominent on the patient's right leg than on her left leg, even though the right leg was operated more than 5 months before the operation on the left leg. The differences of the two legs in the flesh and in 3-D were even more striking than in the photographs.

A formal 20-patient clinical study was performed to determine the effect of a glycerophosphate salt, such as CGP, on surgical wounds resulting from double knee replacement operations. FIGS. 2a, 2b, 2c and 2d, which are black and white photocopies of the color photographs of the knees of one of the 20 human subjects, illustrate the exemplary results from the clinical study. The subject received simultaneous bilateral total knee replacements. With the doctor's approval, his right leg (on the left side of the photographs) was treated with AkPharma's Cellerity® 10 topical lotion (10% (w/w) calcium glycerophosphate formulation, pH 5.65) approximately 72 hours post operation. His left leg (on the right side of the photographs) received no CGP treatment. Since the commencement of the treatment, 2 ml of Cellerity® 10 lotion was topically applied to the wounds of the knee surgeries twice daily everyday and will continue for 6 consecutive weeks.

Figure 2A:
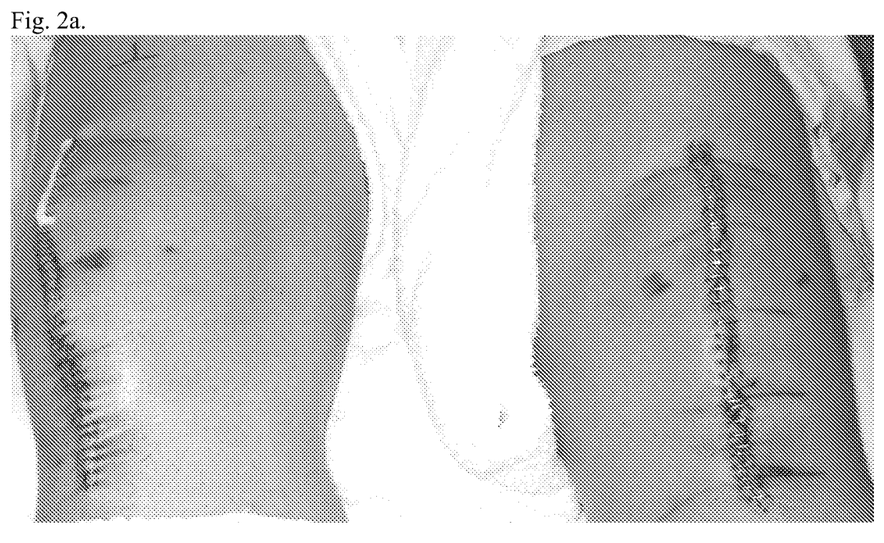
FIG. 2a shows his legs 72 hours post operation, where CGP (in white) was applied to the top portion of the wound on his right leg before it was spread over the entire wounded area.
Figure 2B:
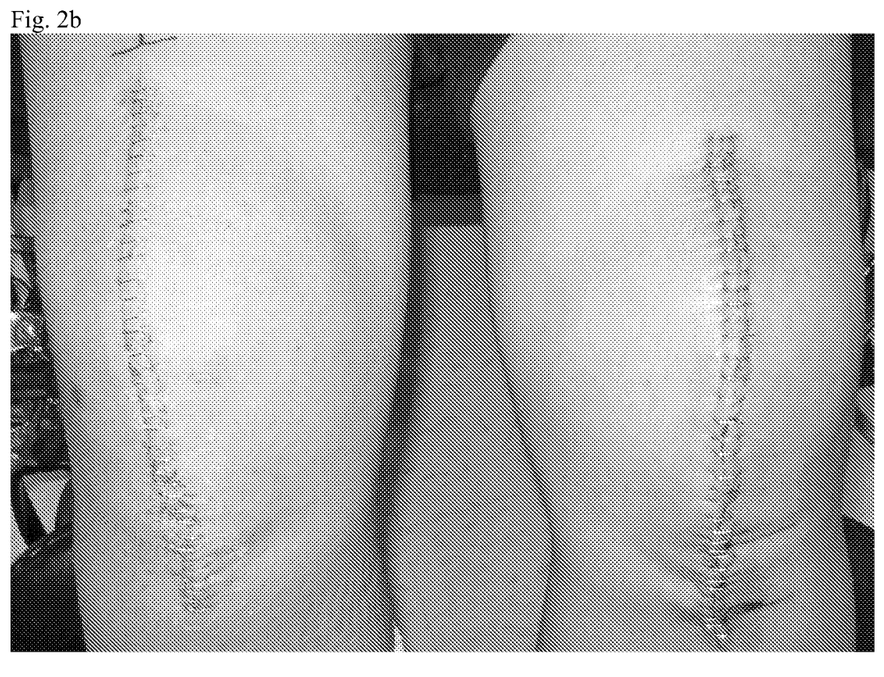
FIG. 2b shows his legs 7 days post operation when staples were still in place.
Figure 2C:
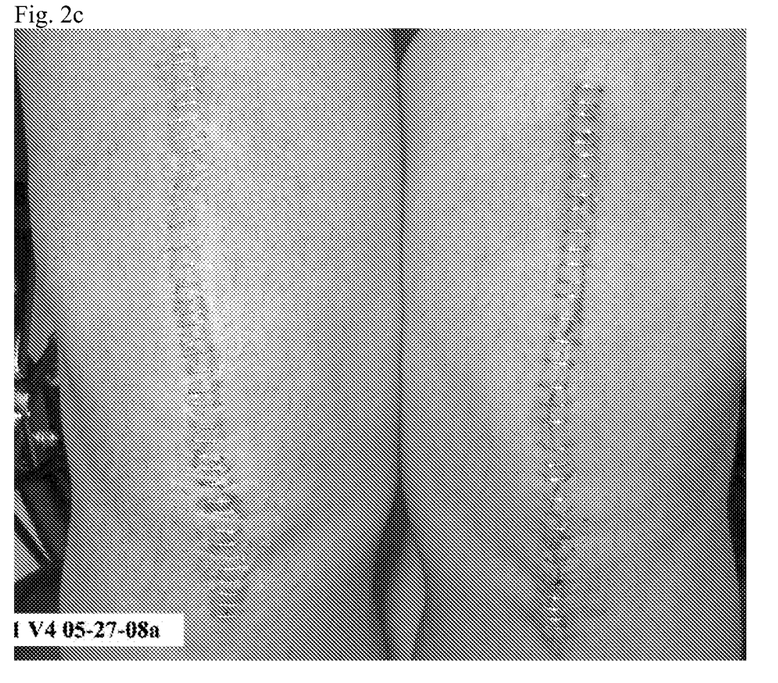
FIG. 2c shows his legs 14 days post operation when staples were still in place.
Figure 2D:
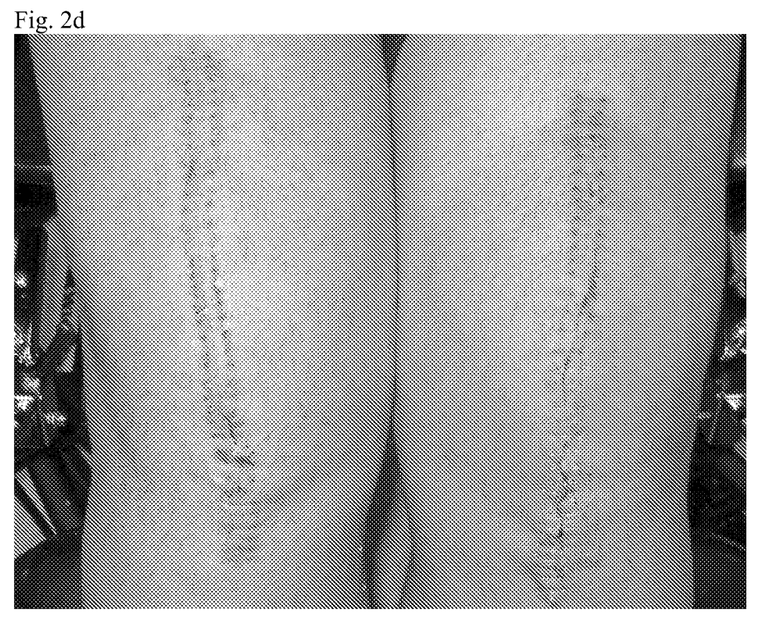
FIG. 2d shows his legs 14 days post operation immediately after staples were removed.

FIG. 2a shows his legs 72 hours post operation, where CGP (in white) is demonstrated as applied to the top portion of the wound on his right leg before more CGP was added to the entire wound and then spread over the entire wounded area. FIG. 2b shows his legs 7 days post operation when staples were still in place. FIG. 2c shows his legs 14 days post operation when staples were still in place. FIG. 2d shows his legs 14 days post operation immediately after staples were removed. The pictures clearly show that the leg treated with CGP has healed dramatically better, almost defying identification of the surgical scar in many locales of the incision. The untreated leg, in contrast, has deep, wandering scars that are almost chasms in their depth and raw openness. In addition, a slight swelling and clearly perceptible continuing pale inflammation over a relatively large area were also observed in the untreated leg, whereas the treated leg showed neither.

In addition, treatment with CGP alleviated the need for application of SteriStrips on the treated leg post staple removal, because wound was deemed sufficiently closed to stay together without external supplemental means or additional assistance. In contrast, SteriStripes were required to be applied to the untreated leg and continued for an additional 7 days.

In addition to surgical wounds resulting from knee replacement operations, methods of the present invention were also evaluated with wounds inflicted by other means.

FIGS. 3a-3f illustrate the wound healing effect of a glycerophosphate salt on wounds resulting from an excision surgery, e.g., to the nose. A female subject received two surgically inflicted wounds to her nose occasioned by removal of benign growths. To investigate the wound healing effect of a glycerophosphate salt, within 24 hours post surgery, one wound was treated with Cellerity® (7.5% (w/w) CGP), while the other only received standard wound treatment. Per physician's request, Neosporin® was applied to both wounds for one week, and Cellerity® was applied topically to the worst of the two wounds, i.e., the left-side surgical wound (on the right side of the photographs), twice daily. The subject was instructed to return to the laboratory for weekly observations.

Figure 3A:
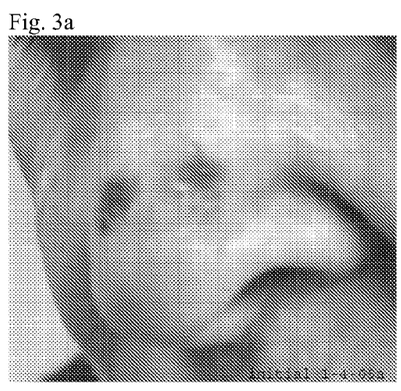
Figure 3B:
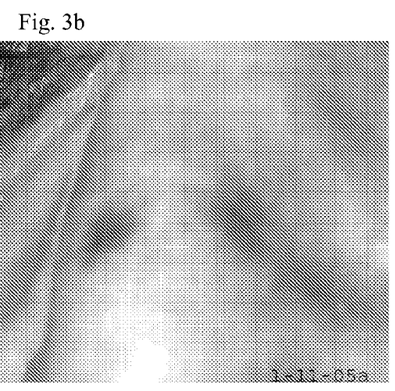
FIG. 3b shows the nose after 7 days of the CGP treatment.
Figure 3C:
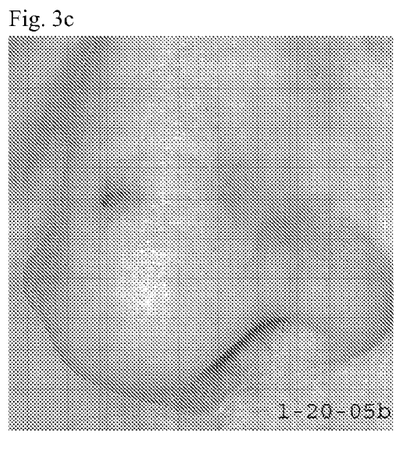
FIG. 3c shows the nose after 16 days of the CGP treatment.
Figure 3D:
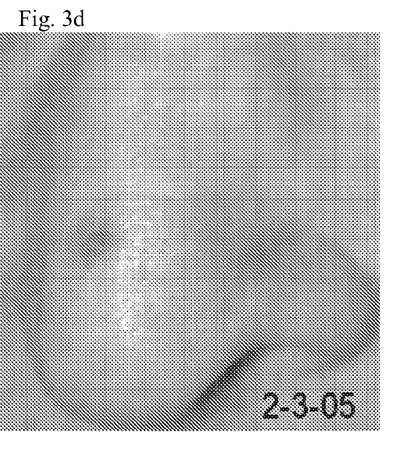
FIG. 3d shows the nose after 30 days of the CGP treatment.
Figure 3E:
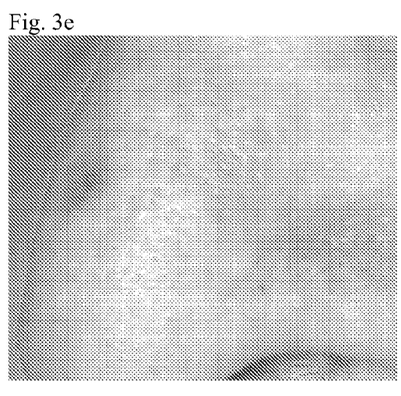
FIG. 3e shows the nose after 37 days of the CGP treatment.
Figure 3F:
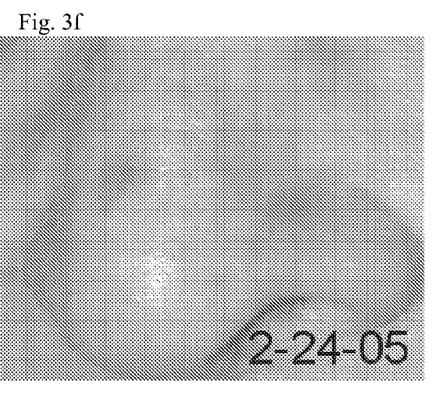
FIG. 3f shows the nose after 51 days of the CGP treatment.
Figure 4A:
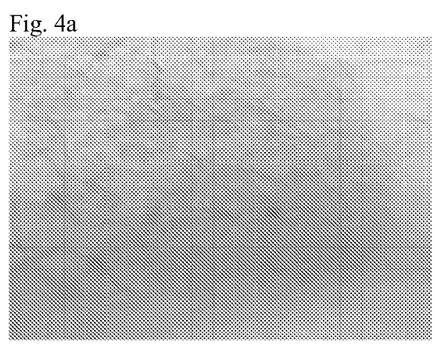
Figure 4B:
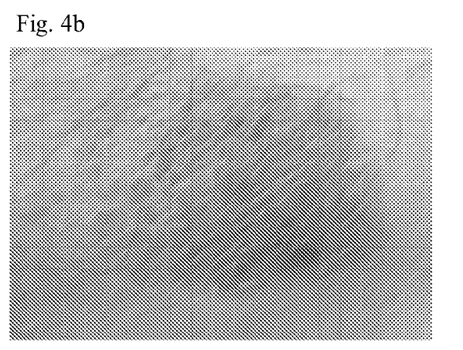
FIG. 4b shows the wound after 3 days of the CGP treatment.
Figure 4C:
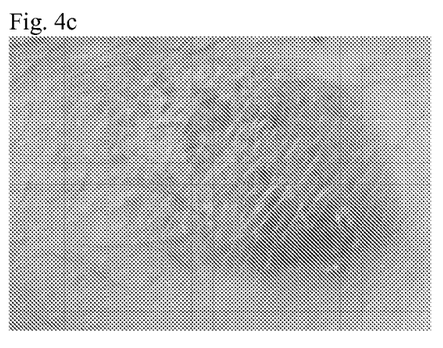
FIG. 4c shows the wound after 5 days of the CGP treatment.
Figure 4D:
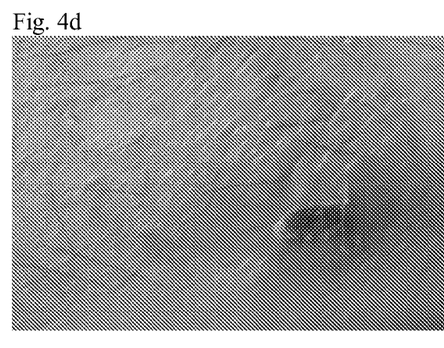
FIG. 4d shows the wound after 9 days of the CGP treatment.
Figure 4E:
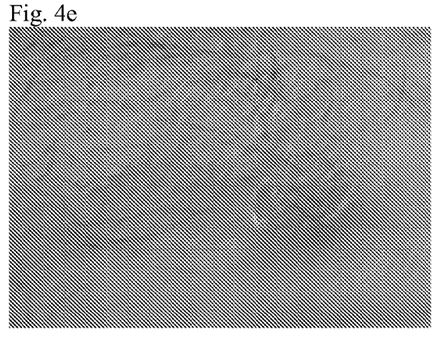
FIG. 4e shows the wound after 13 days of the CGP treatment.
Figure 4F:
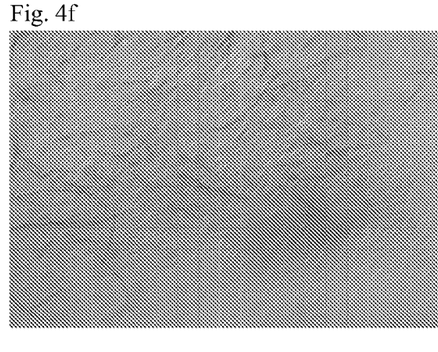

FIG. 3a shows the nose on the day of the surgery, where the left-side wound was deeper than the right-side wound. After one day of the CGP treatment, the subject called and reported almost immediate apparent change in wound healing in favor of the CGP treated site. FIG. 3b shows the nose after 7 days of the CGP treatment, where both wounds were still red, but dryer: the left-side CGP treated-wound appeared less deep than it was a week ago and margins between the wound and undamaged skin became blending; and the right-side wound that received no CGP treatment did not appear to have much change in wound depth, although inflammation was marginally lessened. FIG. 3c shows the nose after 16 days of the CGP treatment: healing of the left-side wound appeared significantly advanced, with epidermal skin recolonized over excised area, and only fading pale pinkish color of healing skin was noted; and healing of the right-side wound was slower and red scab was formed. FIG. 3d shows the nose after 30 days of the CGP treatment: the left-side wound was healed, fully recolonized with epidermal skin, damage was almost unnoticeable, and no scab had been formed since the treatment; and the right-side wound was still open with small inner scab and red encirclement, and it had scabbed 3 times since the treatment. FIG. 3e shows the nose after 37 days of the CGP treatment: the left-side wound was completely healed, while the right-side wound was still present with small inner scab and red encirclement. FIG. 3f shows the nose after 51 days of the CGP treatment: the left-side wound was completely healed, while the right-side wound was still present with small inner scab and red encirclement.

FIGS. 4a-4f illustrate the wound healing effect of a glycerophosphate salt on a burn wound to the inner forearm of a male human subject. He received topical treatment with CGP only to the right-side of the wound (on the left side of the photographs) 24 hours post wound infliction, twice daily. The right-side of the wound was treated topically with Cellerity® lotion (7.5% (w/w) CGP) for the first three days. From day 4 of the treatment, the right-side of the wound was treated with 37% (w/w) CGP content paste. The left-side of the wound received no treatment.

As shown in FIG. 4a-4f, the wound healing improvement effect of CGP was observed as early as 3 days after the treatment. The right-side of the wound was completely healed and disappeared after 16 days of the CGP treatment, while the untreated, left-side of the wound still had a pinkish color.

Figure 5A:
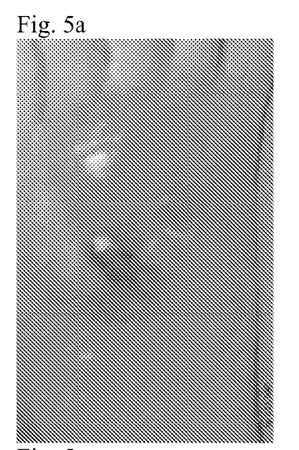
FIG. 5a shows the wound prior to the treatment.
Figure 5B:
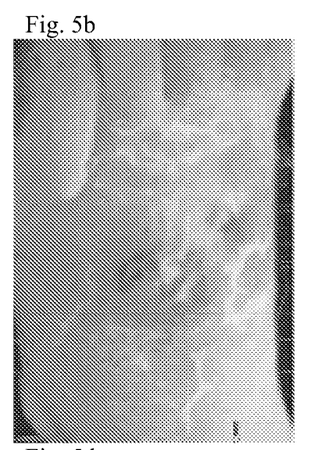
FIG. 5b shows the wound after 18 days of the CGP treatment.
Figure 5C:
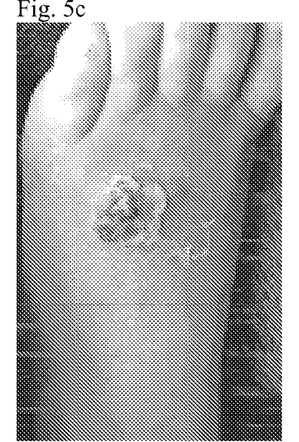
FIG. 5c shows the wound after 39 days of the CGP treatment.
Figure 5D:
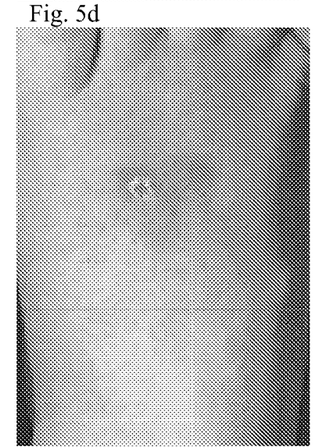
FIG. 5d shows the wound after 50 days of the CGP treatment.

FIGS. 5a-5e illustrate the wound healing effect of a glycerophosphate salt on a spider bite wound to the foot of a male subject. The subject suffered an apparent severe spider bite of his foot with necrosis. The necrosis area was about 3 cm in diameter prior to the treatment (FIG. 5a). A skin graft was initially considered to compensate for the clearly necrotic/dead tissue. After 5 weeks of treatment with a lotion comprising 6.75% (w/w) CGP twice daily, the necrosis area was reduced to 9 mm, and the wound was healed 90% with minimal scarring (FIG. 5c). The observing physician commented that the wound healed at least 50% faster than expected and that the minimal scarring (FIGS. 5d and 5e) was unexpected with this type of wounds.

The studies described above clearly demonstrated that promptly after the infliction of a wound, the earlier treatment of a wound with a glycerophosphate salt, such as CGP, significantly improved wound healing and drastically reduced scar formation, regardless of the type of wound injury.

The following experiment shows the analgesic effect of topical application of a formulation comprising a glycerophosphate salt, namely calcium glycerophosphate, to a human subject. A human subject suffered from an unintentionally inflicted wound on his arm. The subject was in significant pain as a result of the wound. Alcohol was first applied to the wound. Subsequently, a generous thick slather of Cellerity® topical lotion (7.5% (w/w) calcium glycerophosphate formulation, pH 5.65) was applied to the wound. The subject reported that the pain ceased completely almost immediately after the application of the composition. Within about an hour after the application of the composition, the subject felt cool in the wounded area and the cool feeling was accompanied by a complete loss of pain.

In addition, two subjects of the first five subjects enrolled in the double knee replacement clinical study described above reported they felt "less heat" in their knee incision site treated with CGP than in the untreated knee site during the early weeks of post operative recovery.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of treating a wound inflicted by a surgery in a subject, the method comprising administering to the wound a composition comprising an effective amount of a glycerophosphate salt to thereby accelerate healing of the surgical wound as compared to an otherwise identical treatment without the effective amount of the glycerophosphate salt.

2. The method of claim 1, wherein the surgical wound is inflicted by a surgical incision, knee replacement operation, or an excision surgery.

3. The method of claim 1, wherein the composition is first administered to the wound about 0 to about 7 days after the wound is inflicted.

4. The method of claim 1, further comprising administering to the subject a composition comprising one or more ingredients selected from the group consisting of an antiseptic, an immediate local anesthetic, and a longer term analgesic.

5. The method of claim 1, wherein the glycerophosphate salt is calcium glycerophosphate.

* * * * *